US011554106B2

(12) United States Patent
Petitjean et al.

(10) Patent No.: US 11,554,106 B2
(45) Date of Patent: Jan. 17, 2023

(54) PREVENTION OF THE RISKS ASSOCIATED WITH DRUG-INDUCED QT INTERVAL PROLONGATION BY USING A SPECIFIC INHIBITOR OF THE PRODUCTION OF ROS OF MIOCHONDRIAL ORIGIN

(71) Applicants: Marc Childs, Paris (FR); Jacque Sauzieres, Dampierre en Yvelines (FR); Olivier Petitjean, Senlis (FR); Guillaume Petitjean, Paris (FR); Elodie Petitjean, Senlis (FR); Grégoire Petitjean, Verrieres le Buisson (FR)

(72) Inventors: Olivier Petitjean, Senlis (FR); Guillaume Petitjean, Paris (FR); Elodie Petitjean, Senlis (FR); Grégoire Petitjean, Verrieres le Buisson (FR)

(73) Assignees: Marc Childs, Paris (FR); Jacque Sauzieres, Dampierre en Yvelines (FR); Oliver Petitjean, Senlis (FR); Guillaume Petitjean, Paris (FR); Elodie Petitjean, Senlis (FR); Grégoire Petitjean, Verrieres le Buisson (FR)

( * ) Notice: Subject to any disclaimer, the term of this patent is extended or adjusted under 35 U.S.C. 154(b) by 176 days.

(21) Appl. No.: 16/492,546

(22) PCT Filed: Mar. 7, 2018

(86) PCT No.: PCT/FR2018/050521
§ 371 (c)(1),
(2) Date: Sep. 9, 2019

(87) PCT Pub. No.: WO2018/161284
PCT Pub. Date: Sep. 13, 2018

(65) Prior Publication Data
US 2021/0052549 A1 Feb. 25, 2021

(30) Foreign Application Priority Data

Mar. 7, 2017 (FR) ...................................... 1751836
Mar. 7, 2017 (FR) ...................................... 1751839

(51) Int. Cl.
A61K 31/385 (2006.01)
A61K 47/55 (2017.01)
A61P 9/06 (2006.01)
A61K 31/222 (2006.01)
A61K 31/4439 (2006.01)
A61K 31/445 (2006.01)
A61K 31/4468 (2006.01)
A61K 31/454 (2006.01)
A61K 31/4709 (2006.01)
A61K 31/496 (2006.01)
A61K 31/5383 (2006.01)
A61K 31/5415 (2006.01)
A61K 45/06 (2006.01)

(52) U.S. Cl.
CPC .......... *A61K 31/385* (2013.01); *A61K 31/222* (2013.01); *A61K 31/445* (2013.01); *A61K 31/4439* (2013.01); *A61K 31/4468* (2013.01); *A61K 31/454* (2013.01); *A61K 31/4709* (2013.01); *A61K 31/496* (2013.01); *A61K 31/5383* (2013.01); *A61K 31/5415* (2013.01); *A61K 45/06* (2013.01); *A61K 47/55* (2017.08); *A61P 9/06* (2018.01)

(58) Field of Classification Search
CPC .......... A61K 31/385; A61K 45/06; A61P 9/06
See application file for complete search history.

(56) References Cited

U.S. PATENT DOCUMENTS

2003/0187067 A1* 10/2003 Christen .............. A61K 31/385
514/513
2011/0245294 A1 10/2011 Paborji et al.

FOREIGN PATENT DOCUMENTS

| CN | 1732926 B | 8/2010 |
| EP | 1645288 A1 | 4/2006 |
| JP | 2003-531172 A | 10/2003 |
| JP | 2010-522773 A | 7/2010 |
| JP | 2016-540781 A | 12/2016 |
| WO | 01/09118 A3 | 2/2001 |
| WO | 2001/080856 A3 | 11/2001 |
| WO | 2009/109501 A2 | 9/2009 |
| WO | 2012/154774 A1 | 11/2012 |
| WO | 2017/042267 A1 | 3/2017 |

OTHER PUBLICATIONS

Bjelakovic et al., Mortality in Randomized Trials of Antioxidant Supplements for Primary and Secondary Prevention Systematic Review and Meta-analysis, JAMA., (2007), vol. 297, No. 8, pp. 872-857.

Goodman et al., The Beta-Carotene and Retinol Efficacy Trial Incidence of Lung Cancer and Cardiovascular Disease Mortality During 6-Year Follow-up After Stopping—Carotene and Retinol Supplements, Journal of the National Cancer Institute, vol. 96, No. 23, (Dec. 2004), pp. 1743-1750.

Gero et al, The Novel Mitochondria-Targeted Hydrogen Sulfide (H2S) Donors AP123 and AP39 Protect Against Hyperglycemic Injury in Microcascular Endothelial Cells in vitro, Parmacological Research, (Nov. 2016), pp. 186-198.

(Continued)

*Primary Examiner* — Alicia L Otton
(74) *Attorney, Agent, or Firm* — TraskBritt

(57) ABSTRACT

A method of treating a subject for reducing the risk of QT space prolongation associated with the intake of a drug known to prolong QT space includes administering to the subject at least one specific inhibitor of mitochondrial ROS production selected from among anethole trithione (ATT), 4-OH-anethole trithione (ATX), and an ATX ester, and administering to the subject the drug known to prolong QT space.

35 Claims, No Drawings

(56) References Cited

OTHER PUBLICATIONS

International Search Report for International Application No. PCT/FR2018/050521, dated Jun. 19, 2018, 5 pages.
International Written Opinion for International Application No. PCT/FR2018/050521, dated Jun. 19, 2018, 10 pages.
Khanna et al., Protective effect of anethole dithiolethione against oxidative stress induced cytotoxicity in human Jurkat T cells. Biochem Pharmacol. vol. 56, No. 1. (Jul. 1998.), pp. 61-69, (abstract only).
Li et al., HPLC determination of 4-hydroxy-anethole trithione in plasma via enzymatic hydrolysis and its application to bioequivalence study, Journal of Pharmaceutical and Biomedical Analysis, vol. 47, Issue 3, (Jul. 15, 2008, pp. 612-617, (abstract only).
Mangum et al., The novel mitochondria-targeted hydrogen sulfide (H2S) donors AP123 and AP39 protect against hyperglycemic injury in microvascular endothelial cells in vitro, Chem. Res. Toxicol., vol. 28, No. 4, (Apr. 20, 2015, pp. 570-584.
Orr et al., Inhibitors of ROS production by the ubiquinone-binding site of mitochondrial complex I identified by chemical screening, Radic Biol. Med., vol. 65, (Dec. 2013), pp. 1047-1059, (abstract only).
Osseni et al., Tacrine-Induced Reactive Oxygen Species in a Human Liver Cell Line: The Role of Anethole Dithiolethione as a Scavenger, Toxicology in Vitro, vol. 13, (1999), pp. 683-688.
Pouzaud et al., Anethole Dithiolethione: and Antioxidant Agetn Against Tenotoxicity Induced by Fluoroquinolones, Pathologi Biologie, vol. 52, (2004), pp. 308-131.
Salimi et al., Toxicity of macrolide antibiotics on isolated heart mitochondria: a justification for their cardiotoxic adverse effect, Xenobiotica, vol. 46, No. 1, (2016), pp. 82-93 (abstract only.
Stoycheva, Margarita, Pesticides in the modern world. Pest control and pesticide exposure and toxicity assessment, InTech Publisher, (2012), pp. 297-322.
Tebourbi et al., Molecular Mechanisms of Pesticide Toxicity, www.InTechopen.com, (2012), pp. 297-322.
Van Noord et al., Drug- and Non-Drug-Associated QT Interval Prolongation, British Journal of Clinical Pharmacology, vol. 70, No. 1, (2009), pp. 16-23.
Won et al., Ketoconazole Induces Apoptosis in Rat Cardiomyocytes Through Reactive Oxygen Species-Mediated Parkin Overexpression, Arch Toxicol, vol. 89, (2015), pp. 1871-1880.
Yu et al.,, An examination of the potential effect of lipids on the first-pass metabolism of the lipophilic drug anethol trithione, vol. 100, Issue 11, pp. 5048-5058, (abstract only).
Japanese Notice of Reasons for Refusal for Application No. 2019-548367 dated Sep. 21, 2021, 5 pages.
Naregal et al., Elevation of Oxidative Stress and Decline in Endogenous Antioxidant Defense in Elderly Individuals with Hypertension, Journal of Clinical and Diagnostic Research, (Jul. 2017), vol. 11, No. 7, pp. BC09-BC12.
Zhao et al., Resveratrol Protects Against Arsenic Trioxide-induced Cardiotoxicity in vitro and in vivo, British Journal of Pharmacology, (2008), vol. 154, pp. 105-113.

\* cited by examiner

PREVENTION OF THE RISKS ASSOCIATED WITH DRUG-INDUCED QT INTERVAL PROLONGATION BY USING A SPECIFIC INHIBITOR OF THE PRODUCTION OF ROS OF MIOCHONDRIAL ORIGIN

CROSS-REFERENCE TO RELATED APPLICATIONS

This application is a national phase entry under 35 U.S.C. § 371 of International Patent Application PCT/FR2018/050521, filed Mar. 7, 2018, designating the United States of America and published as International Patent Publication WO 2018/162845 A1 on Sep. 13, 2018, which claims the benefit under Article 8 of the Patent Cooperation Treaty to French Patent Application Serial No. FR17/51836, filed Mar. 7, 2017 and French Patent Application Serial No. FR17/51839, filed Mar. 7, 2017.

TECHNICAL FIELD

The present disclosure concerns the prevention and/or treatment of diseases involving reactive oxygen species (or ROS) of mitochondrial origin. It specifically concerns the use of an inhibitor of mitochondrial ROS production, in particular, anethole trithione, to prevent the risks associated with QT prolongation when taking drugs known to induce such a side effect.

BACKGROUND

Mitochondria are involved in the pathogenesis of almost all age-related diseases, including cardiovascular diseases, neurodegenerative diseases (Parkinson's disease, Alzheimer's disease, etc.), diabetes, as well as ischemic tissue dysfunctions. It is widely accepted that it plays a central role in the "free radical theory of ageing." This theory states that the accumulation of damage caused by ROS (for reactive oxygen species) affects many cellular functions, particularly mitochondrial functions that are essential for energy supply and proper functioning of the cells. Mitochondria therefore appear as the primary targets of ROS because optimal cellular functioning is crucial to provide the energy a cell needs to repair itself.

While mitochondria are the main source of ROS, they are also particularly sensitive to damage caused by ROS. As a result, mitochondria themselves generate the ROS that cause oxidative damage to them and contribute to their dysfunction, later on, and to cellular death.

Many studies have been conducted to evaluate the ability of antioxidants to counteract the effect of ROS. Several antioxidant molecules have been shown to be satisfactory in preclinical studies, but their efficacy has only been partially confirmed in most clinical trials (Orr et al., Free Radie. Biol. Med, 2013, 65:1047-59).

In addition, recent studies have shown that too much reduction in ROS has a deleterious effect on cells, suggesting that a balanced production of ROS contributes to good cellular functioning (Goodman et al., J. Natl. Cancer Inst., 2004, 96:1743-50; Bjelakovic G. et al., JAMA. 2007, 297: 842-57).

BRIEF SUMMARY

Research on the role of oxidative stress in many diseases has highlighted the importance of having a selective inhibitor of the mitochondrial production of ROS. The antioxidants available today do not have such specificity and, as a consequence, the risk of side effects when cytosolic ROS production is increased, especially in the case of prolonged treatment; these side effects are well described.

A number of therapeutic families may be responsible for QT prolongation, including antiarrhythmic, antihistamine, antibiotic, antimalarial and psychoactive drugs. This electrocardiographic abnormality can cause ventricular arrhythmia that can lead to sudden death.

Among the drugs that can lead to QT prolongation, fluoroquinolones (FQ), some anti-tuberculosis drugs used in cocktails to treat multi-resistant tuberculosis, in particular, the now classic combination of moxifloxacin, bedaquillin and clofazimine, macrolides and, above all, erythromycin in case of IV administration, imidazole antifungals, such as ketoconazole, as well as Trisenox® indicated for the treatment of promyelocytic leukaemias and antiarrhythmics such as Sotalol® or Cordarone® can be mentioned. This list is not exhaustive, and includes, in particular:

Alfuzosin, Amantadine, Amiodarone, Amisulpride, Amitriptyline, Amphotericin B, Anagrelide, Apomorphine, Aripiprazole, Asenapine, Astemizole, Atazanavir, Atomoxetine, Azithromycin, Bedaquiline, Bendamustine, Bendroflumethiazide, bendrofluazide, Benperidol, Bepridil, Betrixaban, Bortezomib, Bosutinib, Buprenorphine, Cabozantinib, Capecitabine, Ceritinib, Chloral hydrate, Chloroquine, Chlorpromazine, Cilostazol, Ciprofloxacin, Cisapride, Citalopram, Clarithromycin, Clofazimine, Clomipramine, Clozapine, Crizotinib, Cyamemazine, Dabrafenib, Dasatinib, Degarelix, Delamanid, Desipramine, Deutetrabenazine, Dexmedetomidine, Diphenhydramine, Disopyramide, Dofetilide, Dolasetron, Domperidone, Donepezil, Doxepine, Dronedarone, Droperidol, Efavirenz, Eliglustat, Epirubicin, Erythromycin, Escitalopram, Esomeprazole, Ezogabine, Retigabine, Famotidine, Felbamate, Fingolimod, Flecainide, Fluconazole, Fluorouracil, Fluoxetine, Flupentixol, Fluvoxamine, Furosemide, Fluphenazine Galantamine, Garenoxacin, Gatifloxacin, Gemifloxacin, Granisetron, Grepafloxacin, Halofantrine, Haloperidol, Hydrochlorothiazide, Hydrocodone, Hydroquinidine, Hydroxychloroquine, Hydroxyzine, Ibogaine, Ibutilide, lloperidone, Imipramine, Indapamide, Inotuzumab ozogamicine, Isradipine, Itraconazole, Ivabradine, Ketanserin, Ketoconazole, Lansoprazole, Lapatinib, Lenvatinib, Leuprolide, Levofloxacin, Levomepromazine, methotrimeprazine, Levosulpiride, Lithium, Loperamide, Lopinavir, ritonavir, Melperone, Mesoridazine, Methadone, Metoclopramide, Metronidazole, Midostaurine, Mifepristone, Mirabegron, Mirtazapine, Moexipril, Moxifloxacin, Necitumab, Nelfinavir, Nicardipine, Nilotinib, Norfloxacin, Nortriptyline, Nusinersen, Ofloxacin, Olanzapine, Omeprazole, Ondansetron, Osimertinib, Oxaliplatin, Oxytocin, Paliperidone, Palonosetron, Panobinostat, Pantoprazole, Papaverine, Paroxetine, Pasireotide, Pazopanib, Pentamidine, Perphenazine, Pilicanide, Pimavanserin, Pimozide, Pipamperone, Piperacillin, Tazobactam, Posaconazole, Primaquine phosphate, Probucol, Procainamide, Promethazine, Propofol, Prothipendyl, Quetiapine, Quinidine, Ranolazine, Ribociclib, Rilpivirin, Risperidone, Romidepsin, Roxithromycin, Saquinavir, Sotalol, Sertindole, Sertalin, Sevoflurane, Solifenacin, Sorafenib, Sparfloxacin, Sulpiride, Sultropride, Sunitinib, Tacrolimus, Tamoxifene, Telaprevir, Telavancin, Telithromycin, Terfenadine, Terlipressin, Terodiline, Tetrabenazine, Thioridazine, Tiapride, Zinc Trioxide, Tipiracil, Trifluridine, Tizanidine, Tolterodine, Toremifene, Torsemide, Trazodone, Trimipramine, Tropisetron, Valbenazine, Vandetanib, Vardenafil, Vemurafenib, Venlafaxine, Voriconazole, Vorinostat, Ziprasidone, Zotepine, Zuclopenthixol, etc. This risk forces some treatments to be abandoned or their dosage to be moderated. Thus:

the treatment of multi-resistant tuberculosis with moxifloxacin-bedaquillin-clofazimine very often leads, due to the occurrence of QT prolongation, to the deprivation of one of the components of the combination, a decision, which is then accompanied by a loss of benefit for the treated subject;

the doses of ofloxacin and levofloxacin are limited by this same risk, whereas simply doubling or tripling the doses would make it possible to "recover" most of the strains of low-level resistant pneumococci;

similarly, the possibility of increasing the dosage of antipseudomonas FQs such as ciprofloxacin or moxifloxacin could restore activity against *Pseudomonas* spp. or *Acinetobacter* spp., for example.

However, everything indicates that QT prolongation, at least drug-induced, is partly, if not entirely, related to the production of mitochondrial ROS, as demonstrated by two recent publications (Salimi A., Eybagi S., Seydi E. et al., Toxicity of macrolide antibiotics on isolated heart mitochondria: a justification for their cardiac adverse effect. Xenobiotica, 2016, 46:82-93; Won K. J., Lee K. P., Yu S. et al., Ketoconazole induces apoptosis in rat cardiomyocytes through reactive oxygen species-mediated parkin overexpression. Arch. Toxicol., 2015, 89:1871-1880). These two publications highlight both the existence of a dose-response relationship (the QT risk increases with both macrolide and ketoconazole doses used) and, also, a protective effect of ROS scavengers such as tiron or tempol, thus confirming the existence of a toxic mechanism relating to ROS production (Won, 2015).

No treatment exists to date to prevent this serious side effect associated with many drugs that can lead to the production of torsades de pointe and to the death of the subject.

In the present disclosure, the inventors propose to reduce the production of ROS at the mitochondrial level in order to reduce the risk of toxicity that can lead to QT prolongation, while avoiding the harmful side effects of non-selective antioxidants. Thus, the inventors have established the interest of administering a specific inhibitor of mitochondrial ROS production, in particular, trithione anethole (ATT), to prevent the risk of drug-induced QT prolongation.

ATT already has a marketing authorization under the brand name Sulfarlem® to increase bile and saliva secretion. It is used to treat difficult digestion and dry mouth. In the 70 years since this product has been marketed in France, no side effects have been reported to date relating to the long-term use of this molecule.

Indeed, the action mechanism of ATT can be deduced from the results of another unpublished experiment to date: the inventors successfully treated a cat with acute organochlorine poisoning. This result demonstrates that the target of ATT is the mitochondrial complex I (or III) or, possibly, the supercomplex I-III, and this in relation to the results described in 2012 by Tebourbi (Tebourbi et al., Molecular mechanism of pesticide toxicity. In: STOYCHEVA M. Ed. Pesticides in the modern world. Pest control and pesticide exposure and toxicity assessment. InTech publisher, 2012, chapter 15.). Knowing that when ROS are overexpressed by mitochondria, this induces a simultaneous overproduction of cytosolic ROS, whose production source is NADPH oxidase (or NOX, usually NOX4 and NOX2), some authors conclude that NOX are the first responsible when in fact mitochondrial production is the culprit (Gosh R. et al., J. Clin. Diagn. Res., 2017, 11: BC09-BC12; Mangum L. C. et al., Chem. Res. Toxicol, 2015, 28: 570-584).

The inventors have therefore established that ATT, unlike conventional antioxidants, acts directly and selectively on mitochondrial ROS production, mainly at the level of complex I (or complex III) of the mitochondrial respiratory chain, sites that are both the main sites of production of ROS and the main sites of mitochondrial dysfunction (Tebourbi O., 2012, see above).

ATT is therefore the first drug for human use authorized by the FDA and EMA that prevents mitochondria from producing ROS at the level of complex I or III of the respiratory chain.

Thus, the present disclosure has a triple advantage:

1) Such a therapeutic approach makes it possible to consider reducing, or even suppressing, the risks of heart attack associated with certain treatments today, since it increases patient safety with respect to drug-induced QT prolongation. It should be noted that some drugs are now only administered in hospitals to monitor cardiac side effects due to the proven risk of QT prolongation in treated patients. The administration of an inhibitor of mitochondrial ROS production could make such hospitalization unnecessary, providing both a gain in comfort for the patient and savings for hospitals.

2) Such an approach also makes it possible to reconsider the upward dosage of certain drugs (by carrying out dose escalation trials) and thus to authorise the prescription of therapeutic doses that are more certainly effective without incurring the risk of QT prolongation for the patient.

3) Such an approach also makes it possible to reconsider the risk-benefit ratio of certain drugs that have been withdrawn from the market due to the prolongation of the QT interval, such as Terfenadine, Sertindole, Astemizole, Grepafloxacine, Droperidol, Levacethylmethadol, Cisapride, Thioridazine.

In addition, ATT has the necessary qualities to address the technical problem of preventing the risk of drug-induced QT prolongation for several reasons.

First of all, ATT is a powerful free radical scavenger and antioxidant with multiple mechanisms of action as shown in a human T cell model (human Jurkat T cells) (Khanna et al., Biochem. Pharmacol. 1998, 56: 61-69). This property allows protection of tenotoxicity caused by FQ (ciprofloxacin, ofloxacin and pefloxacin) in a tendon cell culture model; a pre-incubation of tenocytes with ATT at a 10 µM concentration for 3 hours significantly reduces the cellular production of ROS and thus protects against oxidative stress induced by FQ. (Pouzaud et al., Path. Biol. 2004, 52: 308-313); this clearly suggests that mitochondrial ROS production is a mechanism of toxicity to FQs and by extrapolation that the QT prolongation observed with different members of this family of antibiotics is most likely a mechanism of the same nature.

On the other hand, ATT is, unlike most other antioxidants, a fat-soluble molecule that confers to it excellent tissue and cell penetration (ADT Vd is, in rats, about 2 L/kg, nearly 10 times the volume of extracellular liquids [Yu H-Z et al., J. Pharm. Sci., 2011, 100:5048-5058]), explaining its access to mitochondria. Thus, ATT acts at micromolar concentrations, 10 µM in Pouzaud's work et al. (2004), a concentration that is easily achieved at the doses usually used; and this molecule appears to have persistent effects over time, certainly for several hours, that should facilitate the administration of the product.

Finally, after administration in both animals and humans, ATT rapidly undergoes demethylation to form a derivative that is itself most likely to be active, 4-OH-anethole trithione (or ATX) that carries an alcohol function on the aromatic ring; this function is esterifiable and can thus give access to water-soluble esters even though ATT and its metabolite ATX are insoluble in water.

The present disclosure proposes, in a very surprising and innovative way, to use this drug in a new therapeutic indication, namely to prevent the risks of drug-induced QT prolongation.

DETAILED DESCRIPTION

A first subject of the present disclosure concerns the use of a specific inhibitor of mitochondrial ROS production to prevent the risk of drug-induced QT interval prolongation.

"Specific inhibitor of mitochondrial ROS production" refers to any compound capable of specifically inhibiting ROS production in the mitochondrial respiratory chain without affecting cellular ROS production in the cytosol; this specificity is essential because it prevents the side effects associated with a ROS defect in the cytosol, as can be observed in the event of excessive inhibition of ROS production by a non-selective antioxidant. In a preferred embodiment, this inhibitor is capable of inducing specific inhibition of ROS production at the level of complex I (or III) of the mitochondrial respiratory chain.

Such inhibitors are, for example, ATT, ATX or NC-POB S, but any other compound with the same inhibitory specificity is appropriate.

In the sense of the present disclosure, the use of "one inhibitor" refers to the use of at least one inhibitor specific to the mitochondrial production of ROS; it may therefore be one inhibitor or a combination of several inhibitors, as described below.

ATT, for anethole trithione, is a 5-(4-methoxyphenyl)-3H-1,2-dithiole-3-thione. It is also known as ADT. Its formula is as follows:

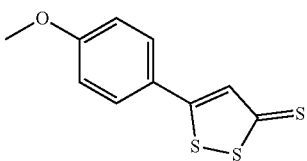

ATX is the phenolic form of ATT as metabolised by the liver, both in humans and animals. This 4-OH-anethole trithione form has been described above (Li et al., J. Pharm. Biomed. Anal., 2008, 47: 612-617). Since the structure of ATT is preserved during this metabolization, there is every reason to believe that the anti-ROS activity of ATT is found in ATX, especially since after oral administration, that is currently the marketed form, most of the circulating product found is ATX (Yu, 2011). In addition, ATX has a para phenol group that allows the formation of esters. In a particular embodiment, ATX is used in its esterified form, for example, as an ester: phosphate, ethylidene phosphate, sulphate, hemisuccinate, acetate, propionate, isobutyrate, hexanoate, pivalate, ethoxycarbonate, nicotinate, or amino acid esters such as glycine, diethylglycine or valine ester, and the list is not exhaustive.

NC-POBS corresponds to N-cyclohexyl-4-(4-nitrophenoxy)benzenesulfonamide, the only molecule described in the literature to date as a specific inhibitor of mitochondrial ROS production at the 1Q site of the respiratory chain (Orr et al., Free Radic. Biol. Med., 2013, 65: 1047-1059).

In a preferred embodiment, the specific inhibitor is chosen from ATT, ATX and an ATX ester. In a particular mode of realization, the prevention of QT prolongation is obtained by combining at least two molecules among ATT, ATX and an ATX ester.

"Drug-induced QT prolongation" refers to a pathological condition characterized by the fact that the QT interval is lengthened following the use of a drug.

The QT interval is one of the electrical data of the electrocardiogram, it corresponds to the electrical duration of the cardiac contraction (systole), the duration of this interval varies with heart rate and with the activity of the autonomic nervous system. The threshold at which QT interval prolongation is likely to degenerate into arrhythmia is not well established. At present, the admitted upper limit is between 420 and 500 ms, depending on age and sex.

The pre-existence of a long QT is, when prescribing certain drugs, a risk factor for serious cardiac rhythm disorders: torsades de pointe may progress to life-threatening ventricular fibrillation.

"Prevention" in the sense of the present disclosure means inhibiting the mitochondrial ROS production before it causes QT prolongation. Prevention also includes reducing the risk of QT prolongation associated with the use of some drugs known to prolong the QT interval and reducing the damage to heart function associated with the use of such drugs. The subject to be treated is preferably a human being.

Thus, the inventors propose to combine the administration of an inhibitor of mitochondrial ROS production with the use of a drug known to promote QT prolongation. The mitochondrial ROS production inhibitor can be administered before or simultaneously with the medication associated with a risk of QT prolongation.

Drugs known to promote QT prolongation include anti-arrhythmic, antihistamine, antibiotic, anti-tuberculosis, anti-malarial, anti-cancer and psychoactive drugs.

In a preferred embodiment, the mitochondrial ROS production inhibitor is associated with a fluoroquinolone (FQ) antibiotic. In particular, ATX or one of its derivatives may be administered with a moxifloxacin-bedaquillin-clofazimine combination or at least one of these antibiotics to prevent QT prolongation when treating multi-resistant tuberculosis. It can also be combined with ciprofloxacin, levofloxacin, moxifloxacin or any other antibacterial FQ, so that its dosage can be increased and resistant strains present at low levels can be "recovered."

In another preferred embodiment, the mitochondrial ROS production inhibitor is combined with arsenic trioxide (Trisenox®) to prevent QT prolongation when treating promyelocytic leukaemias.

In another preferred embodiment, the mitochondrial ROS production inhibitor is combined with antiarrhythmics such as sotalol hydrochloride (Sotalol®) or amiodarone (Cordarone®) to prevent QT prolongation in the prevention of recurrences of some tachycardias.

In another preferred embodiment, the mitochondrial ROS production inhibitor is associated with a drug known to prolong the QT interval selected from the following list: Alfuzosin, Amantadine, Amiodarone, Amisulpride, Amitriptyline, Amphotericin B, Anagrelide, Apomorphin, Aripiprazole, Asenapine, Astemizole, Atazanavir, Atomoxetine, Azithromycin, Bedaquilin, Bendamustine, Bendroflumethiazide, bendrofluazide, Benperidol, Bepridil, Betrixaban, Bortezomib, Bosutinib, Buprenorphin, Cabozantinib, Capecitabin, Ceritinib, Chloral hydrate, Chloroquine, Chlorpromazine, Cilostazol, Ciprofloxacin, Cisapride, Citalopram, Clarithromycin, Clofazimine, Clomipramine, Clozapine, Crizotinib, Cyamemazine, Dabrafenib, Dasatinib, Degarelix, Delamanid, Desipramine, Deutetrabenazine, Dexmedetomidine, Diphenhydramine, Disopyramide, Dofetilide, Dolasetron, Domperidone, Donepezil, Doxepine, Dronedarone, Droperidol, Efavirenz, Eliglustat, Epirubicin, Erythromycin, Escitalopram, Esomeprazole, Ezogabine, Retigabine, Famotidine, Felbamate, Fingolimod, Flecainide, Fluconazole, Fluorouracil, Fluoxetine, Flupentixol, Fluvoxamine, Furosemide, Fluphenazine Galantamine, Garenoxacine, Gatifloxacin, Gemifloxacin, Granisetron, Grepafloxacin, Halofantrine, Haloperidol, Hydrochlorothiazide, Hydrocodone, Hydroquinidine, Hydroxychloroquine, Hydroxyzine, Ibogaine, Ibutilide, Iloperidone, Imipramine, Indapamide, Inotuzumab ozogamicine, Isradipine, Itraconazole, Ivabradine, Ketanserine, Ketoconazole, Lansoprazole, Lapatinib, Lenvatinib, Leuprolide, Levofloxacin, Levomepromazine, methotrimeprazine, Levosulpiride, Lithium, Loperamide, Lopinavir, Ritonavir, Melperone, Mesoridazine, Methadone, Metoclopramide, Metronidazole, Midostaurin, Mifepristone, Mirabegron, Mirtazapine, Moexipril, Moxifloxacin, Necitumumab, Nelfinavir, Nicardipine, Nilotinib, Norfloxacin, Nortriptyline, Nusinersen, Ofloxacin, Olanzapine, Omeprazole, Ondansetron, Osimertinib, Oxaliplatin, Oxytocin, Paliperidone, Palonosetron, Panobinostat, Pantoprazole, Papaverine, Paroxetine, Pasireotide, Pazopanib, Pentamidine, Perphenazine, Pilsicanide, Pimavanserine, Pimozide, Pipamperone, Piperacilline, Tazobactam, Posaconazole, Primaquine phosphate, Probucol, Procainamide, Promethazine, Propofol, Prothipendyl, Quetiapine, Quinidine, Ranolazine, Rib ociclib, Rilpivirine, Risperidone, Romidepsine, Roxithromycin, Saquinavir, Sotalol, Sertindole, Sertalin, Sevoflurane, Solifenacin, Sorafenib, Sparfloxacin, Sulpiride, Sultropride, Sunitinib, Tacrolimus, Tamoxifene, Telaprevir, Telavancin, Telithromycin, Terfenadine, Terlipressine, Terodiline, Tetrabenazine, Thioridazine, Tiapride, Zinc Trioxide, Tipiracil, Trifluridine, Tizanidine, Tolterodine, Toremifene, Torsemide, Trazodone, Trimipramine, Tropisetron, Valbenazine, Vandetanib, Vardenafil, Vemurafenib, Venlafaxine, Voriconazole, Vorinostat, Ziprasidone, Zotepine, and Zuclopenthixol.

In a preferred embodiment, the specific inhibitor of mitochondrial ROS production described in the above-mentioned applications is trithione anethole (ATT) used as monotherapy.

In another preferred embodiment, the daily dose of trithione anethole when used for reducing the risk of QT prolongation associated with taking a drug known to lengthen the QT interval, is between 40 and 400 mg. Preferably, the daily dose is between 80 and 240 mg.

In an even more preferred embodiment, the daily dose of trithione anethole is divided into two doses of 20 to 200 mg each, even more preferably into two doses of 40 to 120 mg each.

For example, each dose may include 40, 50, 60, 70, 80, 90, 100, 110, 120, 150 or 200 mg of ATT.

In a preferred embodiment, the dose of trithione anethole is 80 mg per dose, or 160 mg per day.

In a particular embodiment, trithione anethole is used as monotherapy to prevent the risk of QT prolongation associated with the use of a drug known to prolong QT interval in a pediatric population. In this particular embodiment, the daily dose of ATT is between 40 and 120 mg. Preferably, the daily dose of trithione anethole for a pediatric population is divided into two doses of 20 to 60 mg of ATT, each depending on the age and weight of the child or teenager.

For example, each child's intake may include 20, 30, 40, 50, 60, 70, 80, 90, 100, 110 or 120 mg of ATT.

The present disclosure also concerns a method of preventing drug-induced QT prolongation by administering a therapeutically effective dose of a specific inhibitor of mitochondrial ROS production to a patient in need.

Another method of carrying out the present disclosure concerns a pharmaceutical composition comprising ATT and/or ATX and/or an ATX ester and a suitable vehicle to prevent drug-induced QT prolongation.

In a preferred embodiment, the present disclosure concerns a pharmaceutical composition comprising (i) ATT and/or ATX and/or an ATX ester and (ii) a drug known to prolong the QT interval, as well as the appropriate excipients.

In an even more preferred embodiment, the present disclosure concerns a pharmaceutical composition comprising ATT and/or ATX and/or an ATX ester and (ii) a drug known to prolong the QT interval selected from the following list: Alfuzosin, Amantadine, Amiodarone, Amisulpride, Amitriptyline, Amphotericin B, Anagrelide, Apomorphine, Aripiprazole, Asenapine, Astemizole, Atazanavir, Atomoxetine, Azithromycin, Bedaquiline, Bendamustine, Bendroflumethiazide, bendrofluazide, Benperidol, Bepridil, Betrixaban, Bortezomib, Bosutinib, Buprenorphine, Cabozantinib, Capecitabine, Ceritinib, Chloral hydrate, Chloroquine, Chlorpromazine, Cilostazol, Ciprofloxacin, Cisapride, Citalopram, Clarithromycin, Clofazimine, Clomipramine, Clozapine, Crizotinib, Cyamemazine, Dabrafenib, Dasatinib, Degarelix, Delamanid, Desipramine, Deutetrabenazine, Dexmedetomidine, Diphenhydramine, Disopyramide, Dofetilide, Dolasetron, Domperidone, Donepezil, Doxepine, Dronedarone, Droperidol, Efavirenz, Eliglustat, Epirubicin, Erythromycin, Escitalopram, Esomeprazole, Ezogabine, Retigabine, Famotidine, Felbamate, Fingolimod, Flecainide, Fluconazole, Fluorouracil, Fluoxetine, Flupentixol, Fluvoxamine, Furosemide, Fluphenazine Galantamine, Garenoxacine, Gatifloxacine, Gemifloxacine, Granisetron, Grepafloxacine, Halofantrine, Haloperidol, Hydrochlorothiazide, Hydrocodone, Hydroquinidine, Hydroxychloroquine, Hydroxyzine, Ibogaine, Ibutilide, Iloperidone, Imipramine, Indapamide, Inotuzumab ozogamicin, Isradipine, Itraconazole, Ivabradine, Ketanserine, Ketoconazole, Lansoprazole, Lapatinib, Lenvatinib, Leuprolide, Levofloxacin, Levomepromazine, methotrimeprazine, Levosulpiride, Lithium, Loperamide, Lopinavir, ritonavir, Melperone, Mesoridazine, Methadone, Metoclopramide, Metronidazole, Midostaurine, Mifepristone, Mirabegron, Mirtazapine, Moexipril, Moxifloxacin, Necitumumab, Nelfinavir, Nicardipine, Nilotinib, Norfloxacin, Nortriptyline, Nusinersen, Ofloxacin, Olanzapine, Omeprazole, Ondansetron, Osimertinib, Oxaliplatin, Oxytocin, Paliperidone, Palonosetron, Panobinostat, Pantoprazole, Papaverine, Paroxetine, Pasireotide, Pazopanib, Pentamidine, Perphenazine, Pilsicainide, Pimavanserine, Pimozide, Pipamperone, Piperacillin, Tazobactam, Posaconazole, Primaquine phosphate, Probucol, Procainamide, Promethazine, Propofol, Prothipendyl, Quetiapine, Quinidine, Ranolazine, Ribociclib, Rilpivirin, Risperidone, Romidepsine, Roxithromycin, Saquinavir, Sotalol, Sertindole, Sertalin, Sevoflurane, Solifenacin, Sorafenib, Sparfloxacin, Sulpiride, Sultropride, Sunitinib, Tacrolimus, Tamoxifene, Telaprevir, Telavancin, Telithromycin, Terfenadine, Terlipressin, Terodiline, Tetrabenazine, Thioridazine, Tiapride, Tipiracil, Zinc trioxide, Trifluridine, Tizanidine, Tolterodine, Toremifene, Torsemide, Trazodone, Trimipramine, Tropisetron, Valbenazine, Vandetanib, Vardenafil, Vemurafenib, Venlafaxine, Voriconazole, Vorinostat, Ziprasidone, Zotepine, Zuclopenthixol and appropriate excipients.

In an even more preferred embodiment, the composition includes (i) ATT and (ii) a drug known to prolong the QT interval, as well as appropriate excipients.

In an even more preferred embodiment, the present disclosure concerns a pharmaceutical composition comprising (i) ATT and (ii) moxifloxacin, as well as the appropriate excipients.

In another embodiment, the present disclosure concerns a pharmaceutical composition comprising (i) ATT and/or ATX and/or an ATX ester and (ii) a drug known to prolong the QT interval that has been withdrawn from the market due to an adverse risk benefit ratio, as well as the appropriate excipients.

This composition should preferably be formulated in a dosage form suitable for oral administration.

In an alternative embodiment, the present disclosure concerns an ester-like chimera formed between ATX and a drug causing QT prolongation (according to the previous list) having a carboxylic acid function.

Chimera, in the sense of the present disclosure, means the conjugation between 4-OH-anethole trithione and the carboxylic acid function of a drug causing QT prolongation, allowing the formation of an ATX ester comprising the drug. The purpose of this chimera is to graft ATX onto the drug causing QT prolongation, in order to give it the preventive effect of ATX on QT prolongation.

In a particular embodiment, the present disclosure concerns a chimera formed between ATX and a drug belonging to the class of fluoroquinolones.

In a preferred embodiment, the present disclosure concerns a chimera formed between ATX and a fluoroquinolone selected from moxifloxacin, ciprofloxacin, levofloxacin or grepafloxacin.

In another embodiment, the present disclosure concerns a pharmaceutical composition comprising a chimera formed between the ATX and a drug causing QT prolongation (according to the previous list) having a carboxylic acid function, and the appropriate excipients.

In a preferred embodiment, the present disclosure concerns a pharmaceutical composition comprising a chimera formed between ATX and a fluoroquinolone, as well as the appropriate excipients.

Such a preferred pharmaceutical composition comprises a chimera formed between ATX and a fluoroquinolone selected from moxifloxacin, ciprofloxacin, levofloxacin or grepafloxacin.

EXAMPLES

Example 1: Impact of ATT on Moxifloxacin-Induced QT Prolongation in Dogs

Principle: This is a single-dose study in dogs to examine the protective effect of ATT on QT prolongation induced by the intravenous (IV) injection of a dose of moxifloxacin, which is considered the reference substance (positive control).

Methodology: This is a cross-over and single-dose study conducted on 4 groups of 4 male Beagle dogs receiving, depending on the group:

Group 1—control group: intraperitoneal injection [i.p.] of the ATT vehicle;
Group 2—ATT, 5 mg/kg, administered i.p.;
Group 3—moxifloxacin, 15 mg/kg, administered as a slow IV injection in 5% lactic acid at 0.5 mL/kg; and
Group 4—an ATT dose of 5 mg/kg is injected i.p. 30 minutes before a slow IV dose of moxifloxacin of 15 mg/kg (see above).

In this study, each dog is equipped with an implantable teletransmitter of the "DSI radio-telemetry transmitter" type allowing continuous ECG recording over 24 hours in 10-minute sequences, including the measurement of PQ, QRS, QT and QTc spaces (correction according to the Van de Water formula), heart rate as well as systolic and diastolic BP and mean BP. ECG analysis is performed using Notocord Systems® ECG51a software and BP analysis using APR30a software, also from Notocord Systems®.

Expected results: The QT and QTc intervals are expected to be significantly increased with moxifloxacin and maintained in the normal range if pre-treated with ATT.

Example 2: Impact of ATT on QT Prolongation Caused by Moxifloxacin in Humans

Principle: Following the 2005 ICH E14 recommendation (FDA, 2005), a TQT study ("through QT study") was conducted in healthy volunteers to evaluate the protective effect of ATT on QT prolongation induced by a single oral dose of 400 mg moxifloxacin.

Methodology: This was a single-dose, cross-over study conducted in healthy volunteers.

The volunteers, 16 men aged 18 to 40, were selected based on the following criteria: medical history, physical examination (including a BMI between 18 and 26 kg/m2), vital signs, clinical examinations, biological check-up and 12-lead ECG.

The selected volunteers were equipped with a Holter ECG for a 24-hour recording.

Four sequences were tested with a 7-day wash-out period between each:
  1st sequence—no treatment was given;
  2nd sequence—each volunteer received a 400 mg oral dose of moxifloxacin;
  3rd sequence—each volunteer took 75 mg of ATT by mouth (3 tablets of Sulfarlem® 25); and
  4th sequence—each volunteer received a 400 mg oral dose of moxifloxacin, 60 minutes after an oral dose of 75 mg ATT (3 tablets of Sulfarlem® 25).

Main evaluation criteria: For each of the successive measurement points ("time point") considered independently, the upper bound of the confidence interval must exclude 10 msec for the "double delta QTcF change from baseline", the QTcF being the QT interval corrected according to the Fridericia formula, considered more appropriate in human clinical terms than the other existing correction formulas.

Expected outcome: that, with ATT, the upper limit of the confidence interval of the effect 15 of moxifloxacin on the QTcF interval returned to the safety zone, i.e., that this upper limit was less than 10 msec.

The invention claimed is:
1. A method of treating ventricular arrhythmia in a subject caused by QT space prolongation induced by an inductive drug, the method comprising:
  administering to the subject a specific inhibitor of mitochondrial ROS production selected from the group consisting of anethole trithione (ATT), 4-OH-anethole trithione (ATX), an ester of ATX, and a combination of any thereof.

2. The method according to claim 1, wherein the specific inhibitor of mitochondrial ROS production is ATT.

3. A method of treating ventricular arrhythmia in a subject caused by QT space prolongation induced by an inductive drug, said drug being selected from the group consisting of alfuzosin, amantadine, amiodarone, amisulpride, amitriptyline, amphotericin B, anagrelide, apomorphine, aripiprazole, asenapine, astemizole, atazanavir, atomoxetine, azithromycin, bedaquiline, bendamustine, bendroflumethiazide, bendrofluazide, benperidol, bepridil, betrixaban, bortezomib, bosutinib, buprenorphine, cabozantinib, capecitabine, ceritinib, chloral hydrate, chloroquine, chlorpromazine, cilostazol, ciprofloxacin, cisapride, citalopram, clarithromycin, clofazimine, clomipramine, clozapine, crizotinib, cyamemazine, dabrafenib, dasatinib, degarelix, delamanid, desipramine, deutetrabenazine, dexmedetomidine, diphenhydramine, disopyramide, dofetilide, dolasetron, domperidone, donepezil, doxepine, dronedarone, droperidol, efavirenz, eliglustat, epirubicin, erythromycin, escitalopram, esomeprazole, ezogabine, retigabine, famotidine, felbamate, fingolimod, flecainide, fluconazole, fluorouracil, fluoxetine, flupentixol, fluvoxamine, furosemide, fluphenazine galantamine, garenoxacin, gatifloxacin, gemifloxacin, granisetron, grepafloxacin, halofantrine, haloperidol, hydrochlorothiazide, hydrocodone, hydroquinidine, hydroxychloroquine, hydroxyzine, ibogaine, ibutilide, lloperidone, imipramine, indapamide, inotuzumab ozogamicine, isradipine, itraconazole, ivabradine, ketanserine, ketoconazole, lansoprazole, lapatinib, lenvatinib, leuprolide, levofloxacin, levomepromazine, methotrimeprazine, levosulpiride, lithium, loperamide, lopinavir, ritonavir, melperone, mesoridazine, methadone, metoclopramide, metronidazole, midostaurin, mifepristone, mirabegron, mirtazapine, moexipril, moxifloxacin, necitumumumab, nelfinavir, nicardipine, nilotinib, norfloxacin, nortriptyline, nusinersen, ofloxacin, olanzapine, omeprazole, ondansetron, osimertinib, oxaliplatin, oxytocin, paliperidone, palonosetron, panobinostat, pantoprazole, papaverine, paroxetine, pasireotide, pazopanib, pentamidine, perphenazine, pilsicanide, pimavanserine, pimozide, pipamperone, piperacillin, tazobactam, posaconazole, primaquine phosphate, probucol, procainamide, promethazine, propofol, prothipendyl, quetiapine, quinidine, ranolazine, ribociclib, rilpivirine, risperidone, romidepsine, roxithromycin, saquinavir, sotalol, sertindole, sertalin, sevoflurane, solifenacin, sorafenib, sparfloxacin, sulpiride, sultropride, sunitinib, tacrolimus, tamoxifene, telaprevir, telavancin, telithromycin, terfenadine, terlipressine, terodiline, tetrabenazine, thioridazine, tiapride, tipiracil, zinc trioxide, trifluridine, tizanidine, tolterodine, toremifene, torsemide, trazodone, trimipramine, tropisetron, valbenazine, vandetanib, vardenafil, vemurafenib, venlafaxine, voriconazole, vorinostat, ziprasidone, zotepine, and zuclopenthixol, wherein the method comprises:
  administering anethole trithione (ATT) to the subject as a monotherapy.

4. The method according to claim 3, wherein ATT is administered to the subject at a daily dose of between 40 and 400 mg.

5. The method according to claim 4, wherein ATT is administered to the subject at a daily dose of between 80 and 240 mg.

6. The method according to claim 4, wherein ATT is administered to the subject at a dose of 80 mg per dose.

7. The method according to claim 5, wherein ATT is administered to the subject at a dose of 80 mg per dose.

8. The method according to claim 1, wherein the drug is an antiarrhythmic drug.

9. The method according to claim 8, wherein the antiarrhythmic drug is selected from the group consisting of amiodarone, disopyramide, dofetilide, flecainide, ibutilide, procainamide, and sotalol.

10. The method according to claim 1, wherein the drug is an antihistamine drug.

11. The method according to claim 10, wherein the antihistamine drug is selected from the group consisting of astemizole, hydroxyzine, and terfenadine.

12. The method according to claim 1, wherein the drug is an antibiotic drug.

13. The method according to claim 12, wherein the antibiotic drug is selected from the group consisting of fluoroquinones, metronidazole, telavancin, telaprevir, Amphotericin B, and pentamidine.

14. The method according to claim 1, wherein the drug is an antimalarial drug.

15. The method according to claim 14, wherein the antimalarial drug is selected from the group consisting of chloroquine, and hydroxychloroquine.

16. The method according to claim 1, wherein the drug is a psychoactive drug.

17. The method according to claim 16, wherein the psychoactive drug is selected from the group consisting of amisulpride, amitriptyline, aripiprazole, asenapine, benperidol, chlorpromazine, citalopram, clomipramine, clozapine, cyamemazine, desipramine, doxepine, droperidol, escitalopram, fluoxetine, flupentixol, fluvoxamine, galantamine, imipramine, indapamide, levomepromazine, levosulpiride, lithium, melperone, mesoridazine, methadone, mirtazapine, nortriptyline, olanzapine, paliperidone, paroxetine, perphenazine, pimozide, pipamperone, primaquine phosphate, prothipendyl, quetiapine, risperidone, sertindole, sulpiride, tetrabenazine, trazodone, trimipramine, venlafaxine, ziprasidone, and zotepine.

18. The method according to claim 1, wherein the drug is an anti-cancer drug.

19. The method according to claim 18, wherein the anti-cancer drug is selected from the group consisting of arsenic trioxyde, bendamustine, cabozantinib, capecitabine, carboplatin, epirubicin, 5-fluorouracil, imatinib, lenvatinib, midostaurin, mobocertinib, necitumumab, tamoxifen, tipiracil, toremifen, and trifluridine.

20. The method according to claim 1, wherein the drug is an anti-tuberculosis drug.

21. The method according to claim 20, wherein the anti-tuberculosis drug is selected from the group consisting of bedaquiline, clofazimine, and delamanide.

22. The method according to claim 2, wherein the drug is an antiarrhythmic drug.

23. The method according to claim 22, wherein the antiarrhythmic drug is selected from the group consisting of amiodarone, disopyramide, dofetilide, flecainide, ibutilide, procainamide, and sotalol.

24. The method according to claim 2, wherein the drug is an antihistamine drug.

25. The method according to claim 24, wherein the antihistamine drug is selected from the group consisting of astemizole, hydroxyzine, and terfenadine.

26. The method according to claim 2, wherein the drug is an antibiotic drug.

27. The method according to claim 26, wherein the antibiotic drug is selected from the group consisting of fluoroquinones of fluoroquinones, metronidazole, telavancin, telaprevir, Amphotericin B, and pentamidine.

28. The method according to claim 2, wherein the drug is an antimalarial drug.

29. The method according to claim 28, wherein the antimalarial drug is selected from the group consisting of consisting of chloroquine, and hydroxychloroquine.

30. The method according to claim 2, wherein the drug is a psychoactive drug.

31. The method according to claim 30, wherein the psychoactive drug is selected from the group consisting of consisting of amisulpride, amitriptyline, aripiprazole, asenapine, benperidol, chlorpromazine, citalopram, clomipramine, clozapine, cyamemazine, desipramine, doxepine, droperidol, escitalopram, fluoxetine, flupentixol, fluvoxamine, galantamine, imipramine, indapamide, levomepromazine, levosulpiride, lithium, melperone, mesoridazine, methadone, mirtazapine, nortriptyline, olanzapine, paliperidone, paroxetine, perphenazine, pimozide, pipamperone, primaquine phosphate, prothipendyl, quetiapine, risperidone, sertindole, sulpiride, tetrabenazine, trazodone, trimipramine, venlafaxine, ziprasidone, and zotepine.

32. The method according to claim 2, wherein the drug is an anti-cancer drug.

33. The method according to claim 32, wherein the anti-cancer drug is selected from the group consisting of arsenic trioxyde, bendamustine, cabozantinib, capecitabine, carboplatin, epirubicin, 5-fluorouracil, imatinib, lenvatinib, midostaurin, mobocertinib, necitumumab, tamoxifen, tipiracil, toremifen, and trifluridine.

34. The method according to claim 1, wherein the drug is an anti-tuberculosis drug.

35. The method according to claim 34, wherein the anti-tuberculosis drug is selected from the group consisting of bedaquiline, clofazimine, and delamanide.

* * * * *

UNITED STATES PATENT AND TRADEMARK OFFICE
CERTIFICATE OF CORRECTION

PATENT NO. : 11,554,106 B2
APPLICATION NO. : 16/492546
DATED : January 17, 2023
INVENTOR(S) : Olivier Petitjean et al.

It is certified that error appears in the above-identified patent and that said Letters Patent is hereby corrected as shown below:

On the Title Page
In ITEM (54), Line 5, change "MIOCHONDRIAL" to --MITOCHONDRIAL--

In the Specification
Column 1, Line 5, change "MIOCHONDRIAL" to --MITOCHONDRIAL--
Column 5, Lines 32-33, change "-NC-POB S" to --NC-POBS--
Column 7, Line 36, change "Rib ociclib" to --Ribociclib--

Signed and Sealed this
Eighteenth Day of July, 2023

Katherine Kelly Vidal
*Director of the United States Patent and Trademark Office*